United States Patent
Miller et al.

(10) Patent No.: US 8,313,501 B2
(45) Date of Patent: Nov. 20, 2012

(54) SURGICAL CUTTING INSTRUMENT

(75) Inventors: Sean Miller, Greenwood, IN (US); Dan C. Ireland, Martinsville, IN (US)

(73) Assignee: Nico Corporation, Indianapolis, IN (US)

(*) Notice: Subject to any disclaimer, the term of this patent is extended or adjusted under 35 U.S.C. 154(b) by 295 days.

(21) Appl. No.: 12/210,081

(22) Filed: Sep. 12, 2008

(65) Prior Publication Data
US 2009/0069831 A1 Mar. 12, 2009

Related U.S. Application Data

(60) Provisional application No. 60/971,653, filed on Sep. 12, 2007.

(51) Int. Cl.
*A61B 17/32* (2006.01)
(52) U.S. Cl. .................................................. 606/171
(58) Field of Classification Search .................. 606/169, 606/170, 171, 167, 45, 185, 179, 172, 159, 606/194; 600/567, 566, 564, 562, 568; 604/22, 604/158–161, 164.01, 165.01, 523; 30/208, 30/241, 386, 293
See application file for complete search history.

(56) References Cited

U.S. PATENT DOCUMENTS

| | | | | |
|---|---|---|---|---|
| 3,995,619 A * | 12/1976 | Glatzer | ......................... | 600/550 |
| 4,552,554 A | 11/1985 | Gould et al. | | |
| 5,360,416 A * | 11/1994 | Ausherman et al. | .......... | 604/272 |
| 5,782,849 A * | 7/1998 | Miller | ......................... | 606/159 |
| 5,800,389 A | 9/1998 | Burney et al. | | |
| 6,258,111 B1 * | 7/2001 | Ross et al. | .................... | 606/171 |
| 6,638,233 B2 * | 10/2003 | Corvi et al. | .................... | 600/564 |
| 2001/0000041 A1 * | 3/2001 | Selmon et al. | ................ | 600/585 |
| 2003/0171694 A1 * | 9/2003 | Casula | ......................... | 600/567 |

* cited by examiner

*Primary Examiner* — Kathleen Sonnett
*Assistant Examiner* — Jocelin Tanner
(74) *Attorney, Agent, or Firm* — Rader, Fishman & Grauer, PLLC

(57) ABSTRACT

A surgical cutting instrument for cutting tissue includes an outer cannula with a cutting opening and a cutting member within the cannula. The cutting member is connected to a source of reciprocation, and as the cutting member reciprocates the cutting member head is guided by a sloped member within the cannula to essentially a zero clearance position relative to a cutting edge of the cutting opening of the cannula. The instrument cleanly severs tissue extending through the cutting opening into the outer cannula.

8 Claims, 4 Drawing Sheets

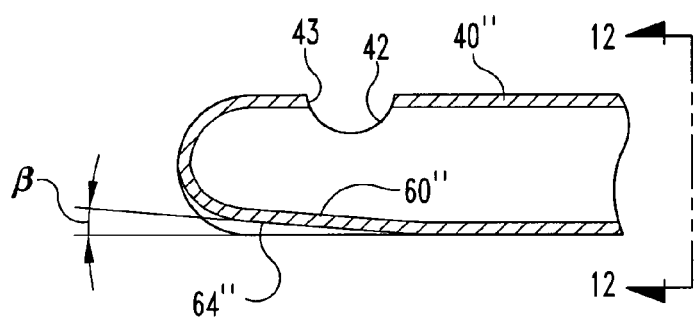 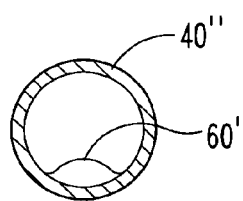
Fig. 11    Fig. 12
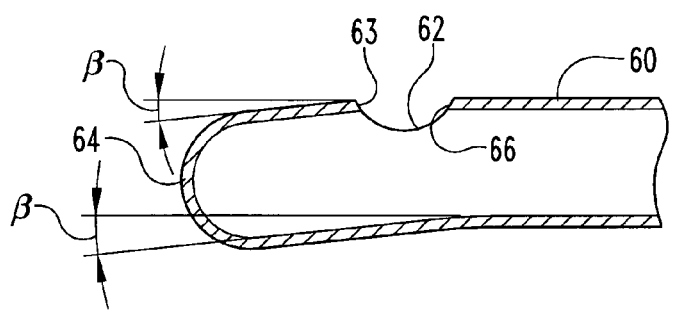
Fig. 13

SURGICAL CUTTING INSTRUMENT

REFERENCE TO RELATED APPLICATION

This application claims priority to provisional application No. 60/971,653 filed on Sep. 12, 2007, the disclosure which is incorporated herein by reference.

BACKGROUND

The present invention relates to surgical cutting instruments, and in particular to cutting instruments configured for use in percutaneous and minimally invasive procedures.

Surgical cutting instruments have been developed that are sized for minimally-invasive or percutaneous access to a site for removal of tissue. One such procedure involves removal of vitreous material from within the eye. Surgical cutting instruments for this type of procedure must have a very small size, because the instrument accesses the interior of the eye directly through the body of the eye. The cutting instruments integrate aspiration with the cutting function to withdraw the tissue as it is excised. In order to accommodate this aspiration function, these cutting instruments are typically of the tube-within-a-tube type in which an inner tubular cutter moves within a larger outer cannula. Vacuum is drawn through the inner tubular cutter to pull tissue severed by the cutter back through the instrument.

Tube-within-a-tube cutting instruments typically incorporate either rotary or reciprocating inner tubular cutters. The rotary cutter includes a cutting edge that rotates past an opening in the outer cannula through which tissue is drawn and severed. In the reciprocating cutter, the inner cutter translates back and forth within the outer cannula. The end of the reciprocating cutter defines a cutting edge that severs tissue extending through the opening in the outer cannula, usually on the forward stroke of the cutter.

In many cases, prior tube-within-a-tube cutters, especially reciprocating cutting instruments, experienced difficulties in cleanly severing target tissue drawn into the opening of the outer cannula. Such difficulties have been manifested in either a failure to actually sever the target tissue, or incompletely cutting the tissue in a given stroke of the inner cutter. In either case, these difficulties significantly compromise the cutting efficiency of the instrument. Difficulties of this type can pose a particularly troublesome problem for certain tissue, such as the vitreous tissue of the eye. A failure to fully sever the target vitreous tissue can lead to "stringers"—vitreous tissue that becomes lodged in the cutting instrument as it is removed from the eye.

In order to address this problem, a "hinged blade" inner cutter was pioneered, as disclosed in U.S. Pat. No. 5,782,849, to Michael E. Miller. General features of this cutting instrument are illustrated in FIGS. 1-5. In particular, the cutting instrument 10 includes a handpiece 12 that supports an outer cannula 20. A tubular inner cutter 22 is disposed for reciprocation within the outer cannula. The cutting head 26 of the inner cutter defines a cutting edge 24 (FIG. 2) that traverses the tissue opening 21 in the outer cannula to sever tissue T. An aspiration vacuum A (FIG. 3) draws a vacuum within the tubular inner cutter through aspiration tube 14. The reciprocating unit reciprocates the inner cutter 22 in the direction R (FIG. 2) by a drive mount 16 connected to a suitable source of linear motion.

As shown in FIG. 3, the outer cannula has an inner diameter $D_1$ greater than the outer diameter $D_2$ of the inner cutter. This difference in diameters provides a running clearance for low friction reciprocation of the inner cutter within the outer cutter. In prior reciprocating cutting instruments, this running clearance was maintained through the entire stroke of the inner cutter, including at the tissue opening 21.

In accordance with one aspect of the invention disclosed in the '849 Patent, a hinge slot 23 is formed in the inner cutter so that the cutting head 26 can pivot in the direction P (FIG. 3) as the cutting edge 24 contacts the tissue T. In other words, as the cutter advances into the tissue T, the tissue tends to resist the forward movement of the cutter. This resistance thus causes the cutting head to pivot in the direction P. As the cutting head 26 pivots upward, it forms an essentially zero clearance between the cutting edge 24 and the edge of the tissue opening in the outer cannula. This zero clearance allows the inner cutter 22 to cleanly sever the tissue segment $T_1$ that has been drawn into the outer cannula. On each stroke of the inner cutter 22, new tissue segments $T_1$ are severed while the vacuum draws previously severed tissue $T_2$ back through the cutting instrument.

Another embodiment of an inner cutter is illustrated in FIG. 4. In this embodiment the hinge slot extends along most of the length of the inner cutter 22' to define a body portion. The cutting head of this embodiment pivots in response to the resistance offered by the tissue, and provide an alternative method of securing the inner cutter to the reciprocating unit.

In a modification of the inner cutter 22, the cutting head 26 may be "pre-bent" at an angle α relative to the length of the tubular inner cutter, as shown in FIG. 5. A user then inserts this "pre-bent" inner cutter into the outer cannula when assembling the cutting instrument 10. It has been found that this "pre-bend" characteristic can optimize the cutting performance of the instrument 10 when operating on difficult tissues. For instance, the vitreous tissue of the eye has viscous properties causing it to offer insufficient resistance to the cutting head 26 as the reciprocating unit advances the inner cutter. In the absence of sufficient resistance from the tissue, the cutting head may not pivot fully upward to form the desired zero clearance. In order to ensure a clean and complete cut, the cutting head 26 is bent upward slightly, as shown in FIG. 5, so that when the cutting edge 24 contacts the tissue at the tissue opening 21, it does so at a nearly zero clearance even in the absence of sufficient resistance from the tissue to cause the cutting head to pivot. A modified inner cutter 22" is shown in FIG. 6 in which the hinge slot 23' is enlarged to optimize the pivot action of the pre-bent cutting head 26.

The pre-bent cutting head shown in FIGS. 2-6 allows the reciprocating cutting instrument to efficiently sever and aspirate a wide range of tissues, including the troublesome vitreous tissue. Moreover, commercial instruments incorporating the hinged-blade and pre-bend features are capable of cutting speeds that greatly exceed the capabilities of prior tube-within-a-tube cutting instruments. However, the pre-bent cutting head shown in FIGS. 5-6 inherently reduces the running clearance between the outer cannula and the inner reciprocating tubular cutter, making contact between the two components more likely. This contact produces sliding friction that can increase the load upon the drive mechanism used to reciprocate the inner cutter. This increased load manifests itself in a reduction in cutting speed or in the need for a larger drive motor. In addition, the sliding friction can generate heat along the length of the instrument, which may not be desirable in certain surgical applications. Therefore, further improvement of this successful cutting instrument is always desirable.

SUMMARY

In order to address this need, the present invention contemplates a surgical cutting instrument that includes a cannula with cutting opening through which tissue enters the internal bore of the cannula. The cannula bore contains a cutting member with a tubular cutting head sized to prevent the cutting head from exiting cutting opening. A source of reciprocating motion reciprocates the cutting member within the cannula past a cutting edge formed on the distal side of the cutting opening. In order to provide for a clean cut, a sloped member disposed in the cannula bore guides the cutting head toward the cutting edge as the cutting head advances toward the distal end of the cannula. The sloped member enables the cutting head and the cutting edge to form a point of essentially zero clearance, thereby cleanly severing any tissue extending through the cutting opening with a scissor-like action. Different embodiments of the slope member are disclosed including a discrete ramp, an indentation, a crease, and an angled distal end of the cannula.

BRIEF DESCRIPTION OF THE DRAWINGS

FIG. 11 is a side cross-sectional view of an outer cannula according to a further embodiment of the invention.

FIG. 12 is an end cross-sectional view of the outer cannula shown in FIG. 11, taken along line 11-11.

FIG. 13 is a side cross-sectional view of another embodiment of the invention.

DETAILED DESCRIPTION

Figure 1:
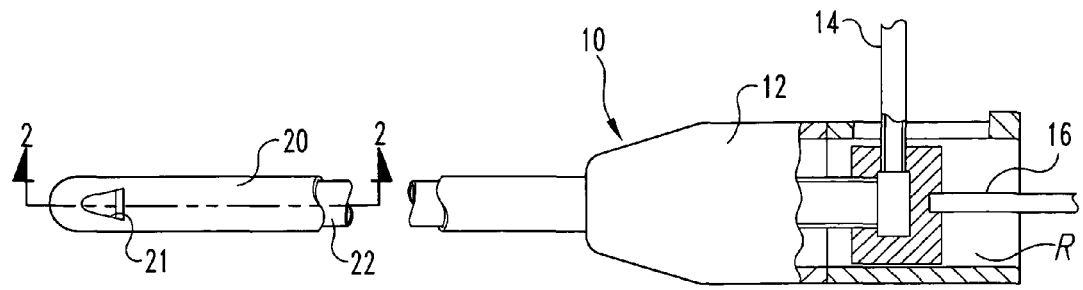
FIG. 1 is a partial cut-away view of the surgical cutting instrument disclosed in U.S. Pat. No. 5,782,849.
Figure 2:
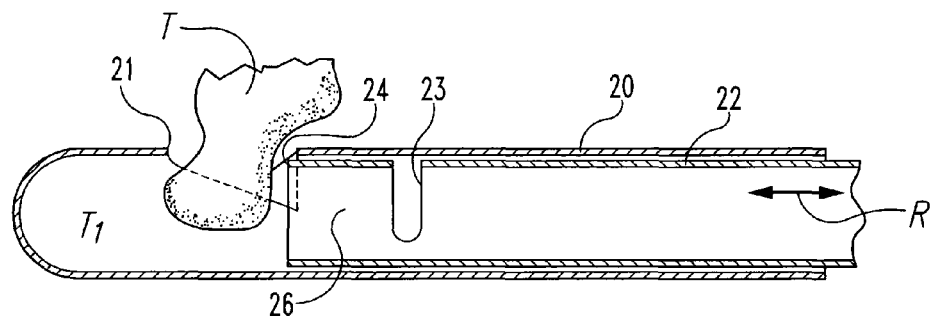
FIG. 2 is a side cross-sectional view of the prior art cutting instrument disclosed in the '849 Patent.
Figure 3:
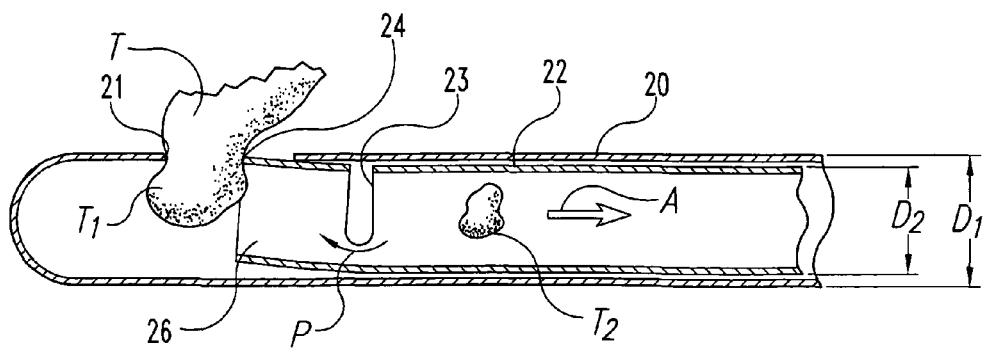
FIG. 3 is a side cross-sectional view of the instrument shown in FIG. 2, with the cutting head depicted in its pivoted "zero clearance" orientation.
Figure 4:
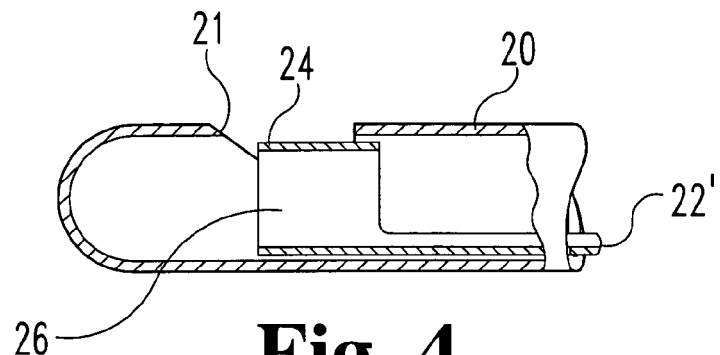
FIG. 4 is a side cross-sectional view of an outer cannula and an alternative inner cutter.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
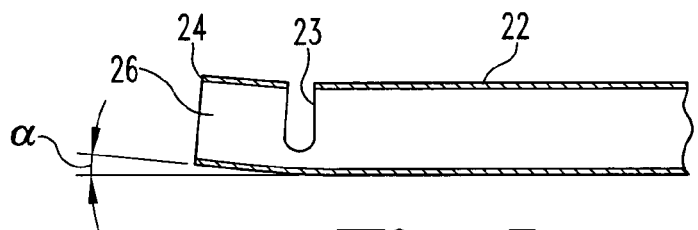
FIG. 5 is a side cross-sectional view of an inner cutter for use with the cutting instrument shown in FIG. 1, with the cutting head being "pre-bent."
Figure 6:
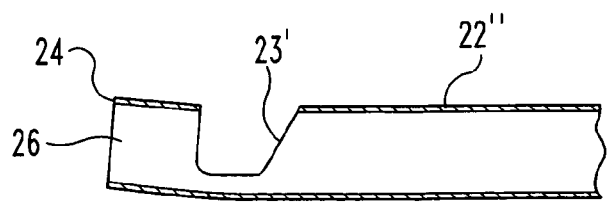
FIG. 6 is a side cross-sectional view of an alternative inner cutter for use with the cutting instrument shown in FIG. 1.

An improved surgical cutting instrument according to the present invention retains the benefits of the running clearance and the hinged cutting head feature of the cutting instrument shown in FIGS. 1-4, as well as the benefits of the "pre-bend" feature of the cutting instrument of FIGS. 5-6. In accordance with embodiments of the present invention, the cutting instrument utilizes a outer cannula 40 with a cutting opening 42 and a sloped member to precisely direct the cutting head 26 to an essentially zero clearance point with cutting edge 43 of the cutting opening 42 so that tissue extending into the cannula 40 can be cleanly cut with a scissor-like action. However, in no embodiment does the cutting head 26 fully exit the cannula 40 through the cutting opening 42. The sloped member contemplates structure that guides the cutting head 26 toward the essentially zero clearance point with the cutting opening 42 including, but not limited to, a ramp 60, an indentation 64, a crease 64", or a bend in the distal end of the cannula 40. It is understood that the sloped member may be located within the outer cannula in orientations and positions that urge or guide the cutting head of the inner cannula toward the cutting edge as the cutting head reciprocates toward the distal end of the cannula. Specific embodiments of the present invention are disclosed below.

Figure 7:
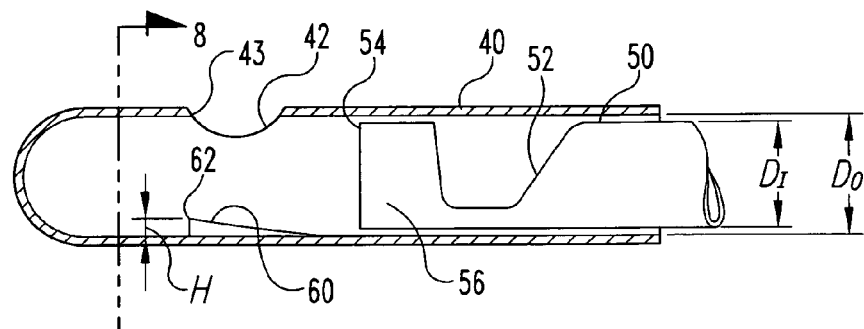
FIG. 7 is a side partial cross-sectional view of an outer cannula and inner cutter according to one embodiment of the present invention.
Figure 8:
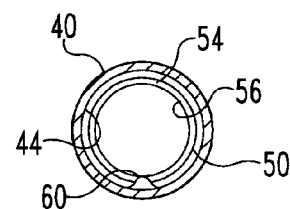
FIG. 8 is an end cross-sectional view of the outer cannula and inner cutter shown in FIG. 7, taken along line 7-7.

One embodiment of the invention shown in FIGS. 7-8, provides an outer cannula 40 with an internal ramp 60 opposing the cutting opening 42. As shown in FIG. 7, the ramp slopes upward toward the end of the outer cannula 40. In one embodiment, the distal end 62 of the ramp is preferably at least coincident with the edge 43 of the opening 42.

The instrument includes a tubular inner cutter 50 that includes a cutting head with a cutting edge 54 arranged to sever tissue extending through the opening 42. The cutter may include a hinge slot 52 so that the cutting head 56 can exhibit the "hinged blade" characteristics of the cutting instrument disclosed in the '849 Patent. Alternatively the cutting head may be connected to a non-tubular body portion or in some embodiments may be a fully tubular body without the "hinged blade" slot provided that the body is capable of deflecting under influence of the sloped member. In these embodiments as the cutting member advances distally toward the opening 42, the cutting head 56 travels up the ramp 60 toward the edge 43 of the cutting opening. The ramp 60 has a height H calibrated in relation to the diameter $D_I$ of the inner cutter 50 and the inner diameter $D_O$ of the outer cannula 40 so that the cutting edge 54 forms an essentially zero clearance at the edge 43 of the opening. Put another way, in certain embodiments the height H of the ramp coincident with the edge 43 of the tissue opening 42 preferably equals the running clearance between the reciprocating inner cutter and the outer cannula 40. In one specific embodiment for a 20 gage cutter, the height H of the ramp is 0.003-0.004 inches with a length of 0.010-0.012 inches. In this specific embodiment, the distal end 62 of the ramp is offset distally from the cutting edge 43 of the opening by 0.000-0.002 inches. Of course, other dimensions of the ramp may be selected based on the running clearance between the inner and outer tubes, the size and location of the tissue opening in the outer cannula, the location of the distal end of the ramp 60 relative to the cutting edge and the stroke of the inner cutter.

As shown in FIG. 8, the ramp 60 preferably includes a semi-circular cross-section along its length, with the apex aligned with the center of the tissue opening 42. Other configurations for the surface of the ramp 60 are contemplated that do not disturb the ability of the inner cutter to slide up the ramp in a stable manner. In order to ensure a precise cut of the tissue, the cutting edge 54 of the inner cutter 50 should be as concentric with the edge 43 of the tissue opening 42 as possible—i.e., the inner cutter should not displace to one side of the outer cannula when the cut is made. In order to maintain this preferred relationship, the surface of the ramp may be slightly concaved at a radius that generally coincides with the diameter $D_I$ of the inner cutter. Moreover, it is preferable for the ramp to be disposed diametrically opposite the cutting opening to ensure a precise scissor action between the edge 54 of the cutting head and the cutting edge 43.

Preferably the ramp defines a linear cross-section in that its height increases uniformly along its length to the distal end 62. However, the ramp may define a nonlinear cross section, such as longitudinally concave, provided that it permits smooth sliding movement of the inner cutter along the ramp, without binding. The ramp shown in FIG. 7 commences slightly before the proximal edge of the tissue opening. However, in other embodiments, the beginning of the ramp may be oriented in a variety of positions relative to the proximal edge of the tissue opening 42.

In the embodiment shown in FIG. 7, the ramp 60 is a separate component from the outer cannula. Thus, the ramp may be attached in a suitable manner to the inner surface of the outer cannula 40, such as by welding or epoxy. Alternatively, a slot (not shown) may be formed in the outer cannula opposite the tissue opening 42 and the ramp may be configured to be mounted within the slot and attached to the outside of the outer cannula.

Figure 9:
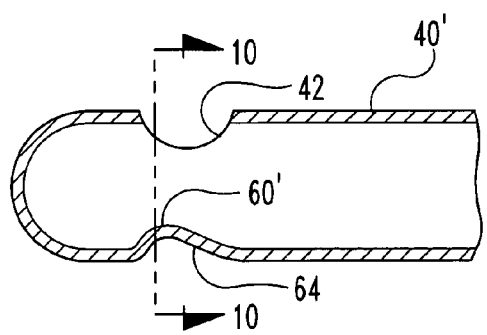
FIG. 9 is a side cross-sectional view of an outer cannula according to a further embodiment of the invention.
Figure 10:
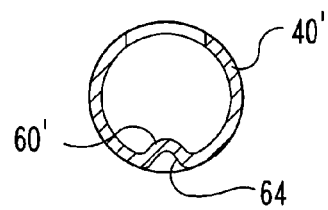
FIG. 10 is an end cross-sectional view of the outer cannula shown in FIG. 9, taken along line 9-9.

In another embodiment, shown in FIGS. 9-10, the shape of the distal end of the outer cannula 40' defines the ramp 60'. In particular, an indentation 64 may be formed in the outer cannula 20 opposite the opening 42. A die or punch may form the indentation 64 in a suitable cold-forming process. In one embodiment the indentation 64 is formed so that the resulting ramp 60' uniformly increases to the preferred height. Alternatively, the indentation could be a circular indentation, a dimple, or a dent so long as when the cutting head 56 contacts the indentation it is guided to a zero clearance position relative the cutting edge 43.

In still another embodiment, the entire distal end of the outer cannula may be creased to form a ramp. Thus, as shown in FIGS. 11-12, the outer cannula 40" includes a ramp 60" defined by a crease 64" at the distal end of the cannula. The crease should be formed at an angle β calibrated to produce the desired cutting clearance between the cutting edge of the inner cutter and the edge 43 of the tissue opening 42. With this embodiment it should be recognized that the stroke of the inner cutter must be controlled so that the cutting head does not travel exceedingly far up the ramp 60" so as to impinge or gall against the outer cannula distal of the edge 43 of the opening.

In the previous embodiments, a ramp, such as ramps 60, 60' and 60", has been provided on the inner surface of the respective outer cannula so that the inner cutter travels up the ramp to achieve the desired cutting clearance. In an alternative embodiment, shown in FIG. 13, the distal end 64 of an outer cannula includes a modification to eliminate the ramp while still retaining the ability for an inner tubular cutter to achieve an essentially zero clearance at the edge 63 of the tissue opening 62. In particular, the distal end is angled relative to the remainder of the outer cannula. The distal end may be bent at an angle β commencing adjacent the proximal edge 66 of the tissue opening 62. With this configuration, the distal edge 63 of the opening is offset at the same angle β relative to the proximal edge. As the inner cutter, such as the cutter 50 shown in FIG. 7, travels toward the distal edge 63, the running clearance decreases until the cutting edge 54 reaches an essentially zero clearance at the distal edge 63.

It is understood that only the preferred embodiments have been presented and that all changes, modifications and further applications that come within the spirit of the invention are desired to be protected. For instance, in the illustrated embodiments, the cutting head 56 is tubular; however, other configurations are contemplated provided that the portion of the cutting edge 54 cooperating with the cutting edge 43 of the outer cannula is sized to span the width of the opening 42 and is configured to follow the shape of the outer cannula 40, 40', 40" at the opening.

We claim:

1. A surgical cutting instrument comprising:
    a cannula having a proximal end and distal end defining a length dimension of said cannula and a central bore along the length of said cannula, said cannula further defining a cutting opening having a first cutting edge adjacent said distal end;
    a handpiece for supporting said cannula at said proximal end;
    a cutting member slidably disposed within said central bore of said cannula, said cutting member having a tubular cutting head portion sized to prevent said tubular cutting head from fully exiting said central bore through said cutting opening, said cutting head portion having a proximal and distal end, said distal end of said cutting head portion defining a second cutting edge, said cutting member also having a body portion between said proximal end of said cutting head portion and said proximal end of said cannula;
    a connecting member within said handpiece for connecting said body portion of said cutting member to a source of reciprocating motion to reciprocate said cutting member within said cannula so that said second cutting edge traverses said first cutting edge; and
    a sloped member separate from the cutting member that is disposed within said cannula, said sloped member defined by a proximal end and a distal end, whereby said sloped member is configured to angle upwardly from the proximal end to the distal end of the sloped member, said proximal end of the sloped member disposed proximally of the cutting opening such that the sloped member begins extending upwardly from the proximal end thereof at a location that is proximal of the cutting opening and wherein said sloped member is positioned relative to said cutting opening to guide said cutting head portion upwardly toward said cutting opening as said cutting head portion advances toward said distal end of said cannula thereby forming an essentially zero clearance between said first and second cutting edges and wherein said sloped member is an indentation protruding into said central bore of said cannula toward said cutting opening, said sloped member has a length extending along a portion of said cannula, a width perpendicular thereto, and a cross section along the width that is semicircular with an apex positioned opposite the cutting opening and centrally positioned along a width of the cutting opening.

2. The surgical cutting instrument according to claim 1, wherein, said cutting member includes a hinge portion between said cutting head portion and said body portion to permit pivoting of said cutting head portion relative said body portion.

3. The surgical cutting instrument according to claim 1, wherein said sloped member is diametrically opposite said cutting opening.

4. The surgical cutting instrument according to claim 1, wherein:
    said cutting opening is further defined by a proximal edge that is positioned opposite said cutting edge and toward said proximal end of said cannula, and
    said sloped member is defined by a portion of said cannula that extends proximally from said proximal edge to said cutting edge of said cutting opening.

5. The surgical cutting instrument of claim 1, wherein:

said central bore and said tubular cutting head define a running clearance dimension therebetween; and said sloped member has a height extending into said central bore that is substantially equal to said running clearance dimension.

6. The surgical cutting instrument of claim 1, wherein the sloped member is integral with the outer cannula.

7. The surgical cutting instrument of claim 1, wherein sloped member uniformly increases to a predetermined height extending from the proximal end of the sloped member to the distal end of the sloped member.

8. The surgical cutting instrument of claim 1, wherein the apex of the sloped member is positioned closer to a distal end of the cutting opening than a proximal end of the cutting opening.

* * * * *